US008700228B2

(12) United States Patent
Tachibana et al.

(10) Patent No.: US 8,700,228 B2
(45) Date of Patent: Apr. 15, 2014

(54) BEAM SCHEDULER AND BEAM ALLOCATION METHOD OF BEAM SCHEDULER

(75) Inventors: Masanori Tachibana, Niihama (JP); Yoshinori Yano, Saijo (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 178 days.

(21) Appl. No.: 13/074,631

(22) Filed: Mar. 29, 2011

(65) Prior Publication Data

US 2012/0253545 A1   Oct. 4, 2012

(51) Int. Cl.
| | |
|---|---|
| H01H 43/00 | (2006.01) |
| G06F 17/00 | (2006.01) |
| H01J 47/00 | (2006.01) |
| G01J 1/42 | (2006.01) |
| G01T 1/00 | (2006.01) |
| G21G 5/00 | (2006.01) |
| A61N 5/00 | (2006.01) |

(52) U.S. Cl.
USPC .......... 700/306; 700/90; 250/492.3; 250/380; 250/394; 250/398

(58) Field of Classification Search
USPC ........................................ 700/306
See application file for complete search history.

(56) References Cited

U.S. PATENT DOCUMENTS

| | | | | |
|---|---|---|---|---|
| 4,123,795 A | * | 10/1978 | Dean et al. ..................... 718/103 |
| 4,857,713 A | * | 8/1989 | Brown ............................... 705/3 |
| 5,260,581 A | * | 11/1993 | Lesyna et al. .............. 250/492.3 |
| 6,464,136 B2 | * | 10/2002 | Walsh ........................... 235/380 |
| 6,830,180 B2 | * | 12/2004 | Walsh ........................... 235/385 |
| 7,936,867 B1 | * | 5/2011 | Hill et al. .................. 379/265.12 |
| 7,937,189 B2 | * | 5/2011 | Tomine ......................... 700/306 |
| 2006/0113487 A1 | * | 6/2006 | Naumann et al. ........... 250/492.3 |
| 2006/0167729 A1 | * | 7/2006 | Rafter et al. ...................... 705/8 |
| 2006/0265351 A1 | * | 11/2006 | Day et al. ......................... 707/2 |
| 2007/0018121 A1 | | 1/2007 | Leyman et al. |
| 2008/0055051 A1 | * | 3/2008 | Snyder et al. ............ 340/286.09 |
| 2012/0102088 A1 | * | 4/2012 | Bindal et al. .................. 709/203 |

FOREIGN PATENT DOCUMENTS

| | | |
|---|---|---|
| JP | 09-233086 A | 9/1997 |
| JP | 2004-267481 A | 9/2004 |
| JP | 2004-329926 A | 11/2004 |
| JP | 2005-182241 A | 7/2005 |
| JP | 2007-501084 | 1/2007 |
| JP | 2008-217325 A | 9/2008 |

OTHER PUBLICATIONS

European Search Report application No. 11002642.4 dated Jul. 29, 2011.

* cited by examiner

*Primary Examiner* — Sean Shechtman
*Assistant Examiner* — Jason Lin
(74) *Attorney, Agent, or Firm* — Squire Sanders (US) LLP

(57) ABSTRACT

A beam scheduler adds the maximum allowable waiting time until a beam is allocated to an irradiation chamber corresponding to an irradiation request when the irradiation request is received from one irradiation chamber of a plurality of irradiation chambers A to D; adds the irradiation request to the end of the order of a waiting list; determines whether or not the predicted waiting time until the beam is allocated to the one irradiation chamber exceeds the maximum allowable waiting time; and advances the order of the irradiation request on the waiting list, thereby allocating the beam to the irradiation chamber corresponding to the top irradiation request in the order of the waiting list, if it is determined that the predicted waiting time exceeds the maximum allowable waiting time.

4 Claims, 6 Drawing Sheets

BEAM SCHEDULER AND BEAM ALLOCATION METHOD OF BEAM SCHEDULER

BACKGROUND

1. Technical Field

The present invention relates to a beam scheduler and a beam allocation method of the beam scheduler which manage allocation of a beam to a plurality of irradiation chambers in a particle beam irradiation facility.

2. Description of the Related Art

As a related art in such a field, there is a system which automatically allocates a particle beam to one of a plurality of irradiation chambers. In this system, if an irradiation request is received from an irradiation chamber in a state where the beam is not allocated to any of the irradiation chambers, the beam is allocated to the irradiation chamber which has issued the irradiation request.

Additionally, in this system, if an irradiation request is received in a state where the beam is already allocated to another irradiation chamber, the irradiation request is arranged on a waiting list according to a priority level which is set in advance, and the beam is allocated according to the order of this waiting list. At this time, if an irradiation request of a higher priority level than the priority level of the irradiation request to which the beam is already allocated is received, allocation of the beam to the irradiation request of the higher priority level is compulsorily performed, on the condition of being before the beam is used.

SUMMARY

According to an embodiment of the invention, there is provided a beam scheduler which manages allocation of a beam to a plurality of irradiation chambers in a particle beam irradiation facility which supplies the beam to one irradiation chamber of the plurality of irradiation chambers. The beam scheduler includes a maximum allowable waiting time addition unit which, if an irradiation request for the beam is received from the one irradiation chamber of the plurality of irradiation chambers, adds the maximum allowable waiting time until the beam is allocated to the one irradiation chamber to the irradiation request; an irradiation request managing unit which adds the irradiation request to the end of the order of a waiting list; a determination unit which determines whether or not the predicted waiting time until the beam is allocated to the one irradiation chamber exceeds the maximum allowable waiting time; and an order changing unit which, if the determination unit has determined that the predicted waiting time exceeds the maximum allowable waiting time, advances the irradiation request up the order of the waiting list. The beam is allocated to the irradiation chamber corresponding to the top irradiation request in the order of the waiting list.

According to an embodiment of the invention, there is provided a beam allocation method of a beam scheduler which manages allocation of a beam to a plurality of irradiation chambers in a particle beam irradiation facility which supplies the beam to one irradiation chamber of a plurality of irradiation chambers, the beam allocation method includes: a maximum allowable waiting time adding step of adding the maximum allowable waiting time until the beam is allocated to the one irradiation chamber to the irradiation request if an irradiation request for the beam is received from the one irradiation chamber of the plurality of irradiation chambers; an irradiation request management step of adding the irradia- tion request to the end of the order of a waiting list; a determination step of determining whether or not the predicted waiting time until the beam is allocated to the one irradiation chamber exceeds the maximum allowable waiting time; an order changing step of advancing the irradiation request up the order of the waiting list if it is determined that the predicted waiting time exceeds the maximum allowable waiting time in the determination step; and an allocation step of allocating the beam to the irradiation chamber corresponding to the top irradiation request in the order of the waiting list.

DETAILED DESCRIPTION

Figure 1:
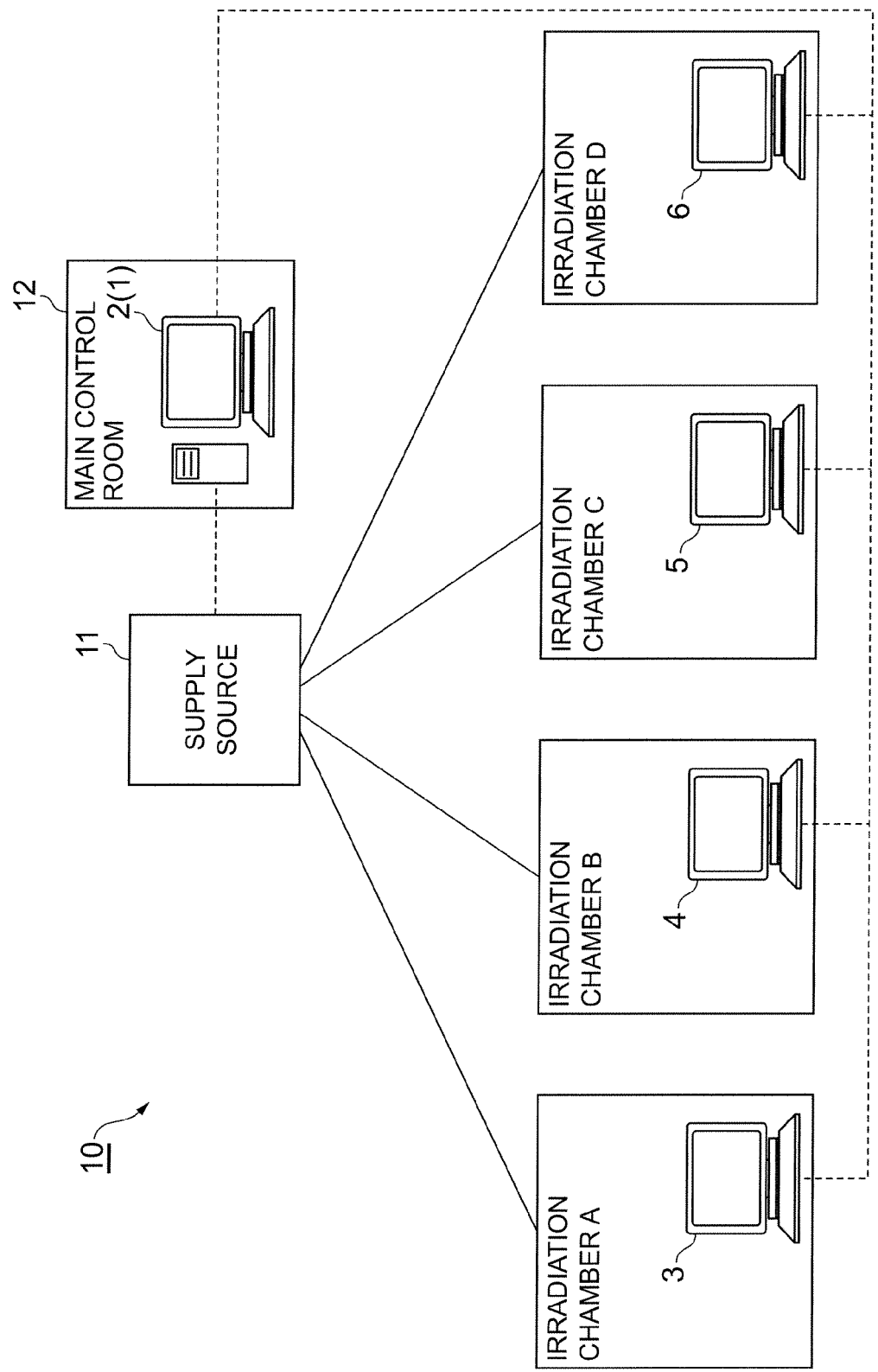
FIG. 1 is a schematic configuration diagram showing a particle beam irradiation facility including a beam, scheduler related to an embodiment of the invention.

In the above system of related art, allocation of the beam to the irradiation request of a lower priority level is postponed whenever an irradiation request with a higher priority level is issued, and the irradiation request of the lower priority level may be kept waiting for a long time. If a patient is kept waiting for a long time in this way, the possibility of an irradiation chamber being occupied, but medical treatment not being performed, and medical treatment being postponed due to a change in patient's condition may be increased. Therefore, there is a problem that efficient utilization of a particle beam irradiation facility is hindered.

Thus, it is desirable to provide a beam scheduler and a beam allocation method of a beam scheduler capable of achieving efficient utilization of a particle beam irradiation facility.

According to the beam scheduler related to the invention, when the irradiation request is received from the irradiation chamber if the beam is allocated, the irradiation request is arranged on the waiting list in received order, and the beam is allocated to the irradiation chamber corresponding to the top irradiation request in the order of the waiting list. Additionally, if it is determined that the waiting time of an irradiation request exceeds the maximum allowable waiting time, a situation where a healthcare practitioner, such as a doctor, or a patient is kept waiting for a long time exceeding the maximum allowable waiting time can be avoided by advancing the irradiation request up the order of the waiting list. Thereby, a situation where medical treatment is postponed due to changes in the patient's condition during prolonged waiting can be avoided, and efficient utilization of the particle beam irradiation facility can be achieved. Moreover, it is possible for a healthcare practitioner to make a prediction about the beam allocation in the maximum allowable waiting time, and prepare medical treatment appropriately. This contributes to an increase in efficiency of utilization of the particle beam irradiation facility.

In the embodiment of the invention, the beam scheduler may further include a request deletion unit which, if a cancellation request is received from the irradiation chamber corresponding to the irradiation request arranged on the waiting list, deletes the irradiation request from the waiting list.

When such a configuration is adopted, if a healthcare practitioner determines that the allocation of the beam to the irradiation chamber is unnecessary, the irradiation request for the irradiation chamber is deleted by sending a cancellation request. Thus, allocation of an unnecessary beam can be avoided.

Additionally, in the beam scheduler related to the embodiment of the invention, if the predicted waiting time of other irradiation requests exceeds the maximum allowable waiting time of above-referenced other irradiation requests due to an advancing procedure of the order of the irradiation request, the order changing unit may extend the maximum allowable waiting time of the irradiation request without the advancing procedure.

In this case, a situation where the predicted waiting time of other irradiation requests exceeds the maximum allowable waiting time by the advancing procedure can be avoided. Additionally, by extending the maximum allowable waiting time so as to have a length equal to or greater than the predicted waiting time of an irradiation request which has higher priority in the order, it is possible for a healthcare practitioner to make a prediction relating to the time when the beam is allocated on the basis of the maximum allowable waiting time after extension.

Moreover, in the beam scheduler related to the embodiment of the invention, if a demoting request which demotes the order of the irradiation request is received from the irradiation chamber to which the beam is allocated, the order changing unit may exchange the order of the irradiation request located at the top of the order of the waiting list, and the position of the irradiation request located next in the order.

In this case, as a demoting request is issued after the beam is allocated, replacement can be made by yielding allocation of the beam to the irradiation chamber of the next order, and thereby the time required for medical treatment can be adjusted. As a result, a situation where the allocation time of the beam is extended for the reason of awaiting the stabilization of a patient's condition and the like can be avoided, and efficient utilization of the particle beam irradiation facility can be achieved.

According to the beam allocation method related to the embodiment of the invention, when the irradiation request is received from the irradiation chamber if the beam is allocated, the irradiation request is arranged on the waiting list in received order, and the beam is allocated to the irradiation chamber corresponding to the top irradiation request in the order of the waiting list. Additionally, if it is determined that the predicted waiting time of an irradiation request exceeds the maximum allowable waiting time, a situation where a healthcare practitioner, such as a doctor, or a patient is kept waiting for a long time exceeding the maximum allowable waiting time can be avoided by advancing the irradiation request up the order of the waiting list. Thereby, a situation where medical treatment is postponed due to changes in a patient's condition during prolonged waiting can be avoided, and efficient utilization of the particle beam irradiation facility can be achieved. Moreover, it is possible for a healthcare practitioner to make a prediction that the beam is allocated in the maximum allowable waiting time, and prepare medical treatment appropriately. This contributes to an increase in efficiency of utilization of the particle beam irradiation facility.

Hereinafter, preferred embodiments of a beam scheduler and a beam allocation method related to the invention will be described in detail with reference to the drawings.

Figure 2:
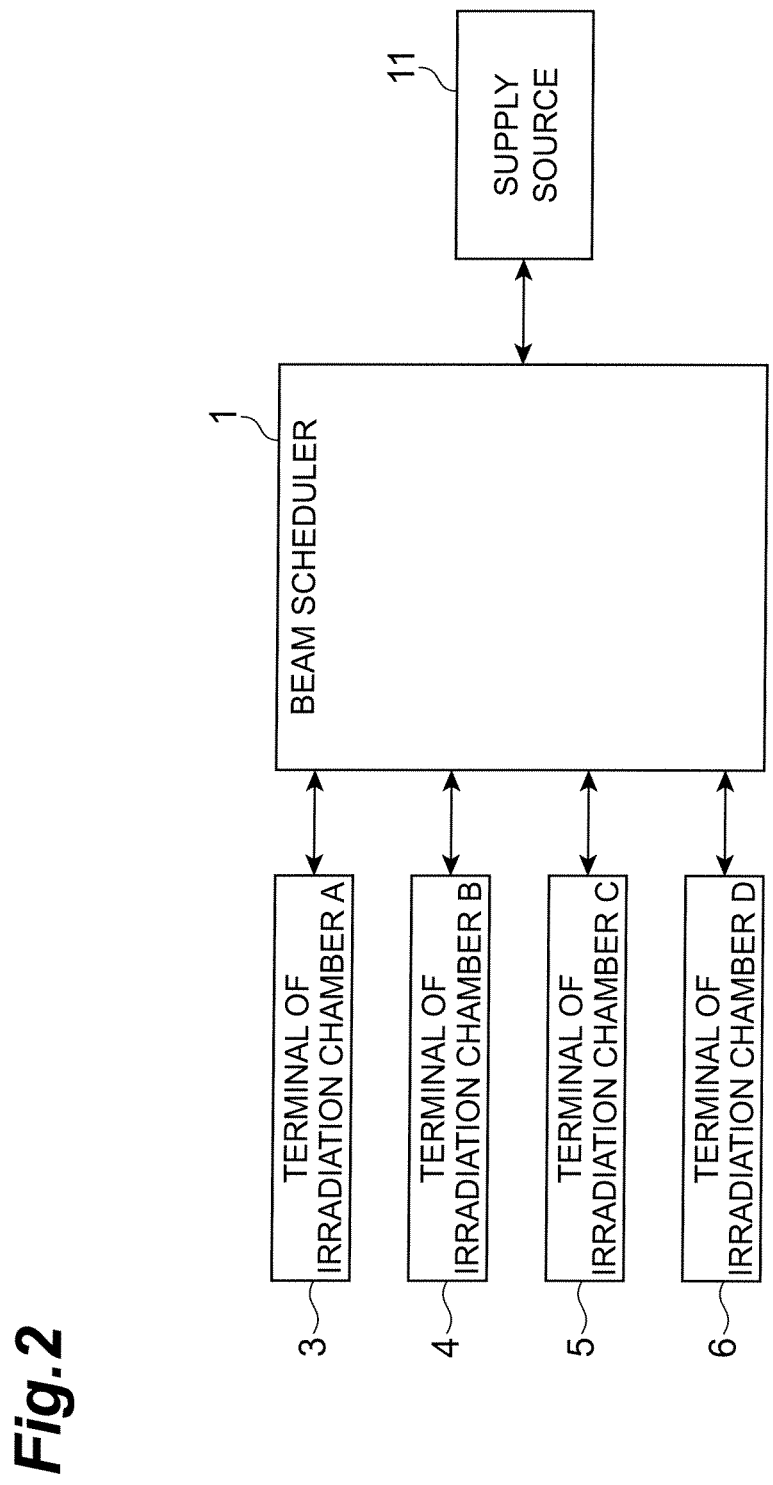
FIG. 2 is a block diagram showing one embodiment of the beam scheduler related to the embodiment of the invention.

As shown in FIGS. 1 and 2, a beam scheduler 1 related to the present embodiment is used within a particle beam irradiation facility 10 which irradiates a tumor inside a patient's body with a particle beam, thereby performing treatment of cancer or the like. The particle beam irradiation facility 10 has a supply source 11 which generates beams, such as a proton beam, a neutron beam, and a carbon ion beam, a main control room 12 where a main control unit 2 which controls the supply source 11 is arranged, and four irradiation chambers A to D where irradiation treatment is performed using a beam supplied from the supply source 11. In addition, the particle beam irradiation facility 10 is not limited to four in the number of irradiation chambers, but may have two or more irradiation chambers.

The supply source 11 of the particle beam irradiation facility 10 is a particle accelerator which accelerates charged particles, such as a cyclotron and a synchrotron. The supply source 11 supplies the beam only to any one of the irradiation chambers A to D. The beam generated in the supply source 11 is guided to an irradiation chamber which is an object to be supplied by a switching electromagnet (not shown) which switches the supply destination of the beam to any one of the irradiation chambers A to D. The supply source 11 and the switching electromagnet are connected to the main control unit 2 via a communication network, and are controlled by a signal sent from the main control unit 2.

The beam scheduler 1 is a portion of the main control unit 2 constituted by one or a plurality of computers, and is configured by utilizing hardware, such as a CPU (Central Processing Unit) and a memory, and software within the main control unit 2. The beam scheduler 1 manages allocation of the beam, which is generated from the supply source 11, to the irradiation chambers A to D. Here, the allocation of the beam to the irradiation chambers is performed by creating a state where one irradiation chamber serving as an object to be supplied occupies the beam generated in the supply source 11, specifically, by controlling equipment, such as an electromagnet, so that supply of the beam to irradiation chambers other than the object to be supplied is blocked, and the beam is guided only to the irradiation chamber which is the object to be supplied.

The beam scheduler 1 is connected to terminals 3 to 6 provided at the irradiation chambers A to D, respectively, via the communication network. In the respective irradiation chambers A to D, irradiation requests $R_A$ to $R_D$ which request allocation of the beam are transmitted to the beam scheduler 1 by inputting the irradiation requests $R_A$ to $R_D$ to the terminals 3 to 6, respectively. In the beam scheduler 1, allocation of the beam is performed on the irradiation chambers A to D corresponding to the irradiation requests $R_A$ to $R_D$ which have been received. In an irradiation chamber to which the beam has been allocated, a patient's medical treatment is performed utilizing the beam supplied from the supply source 11. Additionally, in the beam scheduler 1, if a beam irradiation end signal has been transmitted from the irradiation chamber to which the beam has been allocated, the irradiation request of the irradiation chamber is deleted, and the beam is allocated to the irradiation chamber corresponding to the next irradiation request. In addition, the beam scheduler 1 has a function of a maximum allowable waiting time addition unit, an irradiation request managing unit, a determination unit, an order changing unit, and a request deletion unit, which are set forth in the claims.

Next, a beam allocation method of the beam scheduler 1 will be described in detail with reference to the drawings. First, processing of the beam scheduler 1 when the irradiation request $R_A$ has been transmitted from the terminal 3 of the irradiation chamber A will be described taking as an example a case where an irradiation request has been received.

Figure 3:
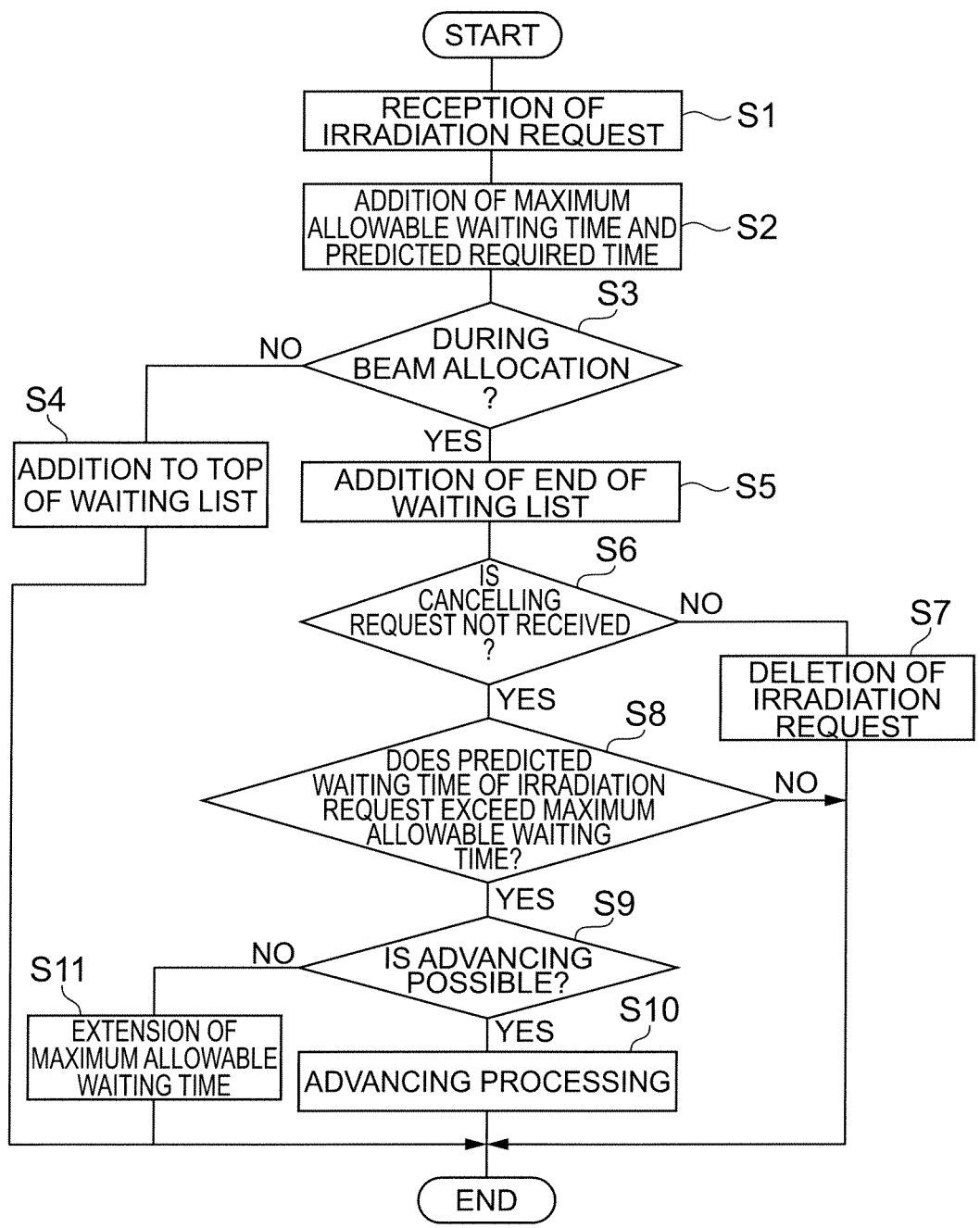
FIG. 3 is a flow chart showing the processing of the beam scheduler when an irradiation request has been received.

As shown in FIG. 3, first, the beam scheduler 1 receives an irradiation request first transmitted from the irradiation chamber A (Step S1). At this time, the beam scheduler 1 receives information on the maximum allowable waiting time and predicted required time which have been input to the terminal 3 of the irradiation chamber A along with the irradiation request $R_A$. Here, the maximum allowable waiting time is the waiting time which is allowable until the beam is allocated to an irradiation chamber after a healthcare practitioner, such as a doctor, issues an irradiation request. Additionally, the predicted required time is predicted time until use of the beam ends after the beam is allocated to an irradiation chamber and then allocation of the beam to the next irradiation chamber is allowed. The predicted required time is set with a sufficient margin so that medical treatment may not be suspended partway through, even when the medical treatment is prolonged.

The maximum allowable waiting time and the predicted required time can be manually set to arbitrary values. For example, if early medical treatment is required according to a patient's condition or the like, the maximum allowable waiting time to be given to an irradiation request can be set to be short. In addition, if setting has not been manually performed, the maximum allowable waiting time and the predicted required time are automatically set by the terminal 3 according to information on the energy and intensity of a beam which are included in the irradiation request.

The beam scheduler 1 adds (associates) the maximum allowable waiting time and the predicted required time to the irradiation request which has been received (Step S2). The Step S2 is equivalent to the maximum allowable waiting time adding step in the claims, and an irradiation request is associated with the maximum allowable waiting time and the predicted required time corresponding to this irradiation request by this step.

Figure 4:
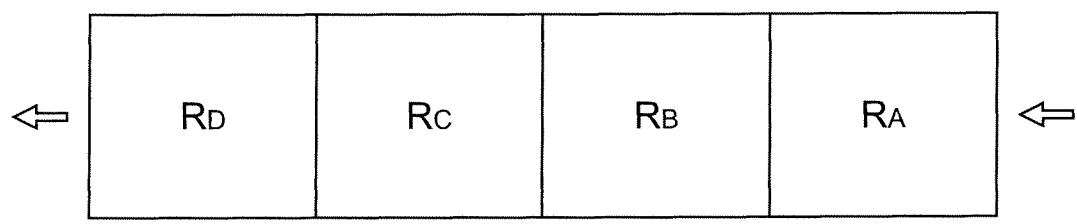
FIG. 4 is a view showing a waiting list.

In Step S3, the beam scheduler 1 determines whether or not the beam is already allocated to the other irradiation chambers B to D (that is, whether or not irradiation requests from the other irradiation chambers B to D exist on the waiting list). Hereinafter, the waiting list will be described. The waiting list is a list in which the irradiation requests corresponding to the irradiation chambers are arranged in order in which the beam is to be allocated. A waiting list when the beam scheduler 1 has received the irradiation requests $R_A$ to $R_D$ in order of the irradiation chamber D, the irradiation chamber C, the irradiation chamber B, and the irradiation chamber A is shown in FIG. 4. In the waiting list shown in FIG. 4, the beam is allocated specifically to the irradiation chamber D of the irradiation request $R_D$ located at the top of the order of the list unless there are other instructions. Thereafter, when the beam irradiation in the irradiation chamber D is ended, the irradiation request $R_D$ is deleted, the irradiation request $R_C$ is located at the top of the waiting list, and allocation of the beam to the irradiation chamber C is performed. In this way, allocation of the beam to an irradiation chamber corresponding to an irradiation request located at the top of the order of the waiting list is performed sequentially.

If the beam scheduler 1 determines that the beam is not allocated to any irradiation chamber (that is, not even one irradiation request exists on the waiting list) in Step S3, the irradiation request $R_A$ is added to the top of the order of the waiting list (Step S4). Thereafter, the beam scheduler 1 ends the processing relating to the irradiation request $R_A$ once.

On the other hand, if the beam scheduler 1 has determined that the beam is allocated (that is, at least one of the irradiation requests $R_B$ to $R_D$ exists) in Step S3, the irradiation request $R_A$ is added to the end of the order of the waiting list (Step S5). This Step S5 is equivalent to an irradiation request management step in the claims.

In addition, an aspect may be adopted in which the aforementioned predicted required time is added to an irradiation request by the beam scheduler 1 in Step S4 or Step S5 in which the predicted required time is to be added to the waiting list. Similarly, an aspect may also be adopted in which the maximum allowable waiting time is added to an irradiation request by the beam scheduler 1 in Step S5. In this case, as for the maximum allowable waiting time, a total of the predicted required time of the irradiation requests $R_B$ to $R_D$ which have higher priority in the order than the irradiation request $R_A$ on the waiting list can be calculated, and the maximum allowable waiting time with a length greater than this total time can be automatically set. In this way, by automatically setting the maximum allowable waiting time to a length greater than the waiting time of the irradiation request $R_A$ which is predicted, it is possible to avoid a situation where a healthcare practitioner or a patient is kept waiting for a long time exceeding the maximum allowable waiting time.

Thereafter, it is determined whether or not the beam scheduler 1 has received a cancellation request from the irradiation chamber A (Step S6). The cancellation request is used if it is intended to cancel the irradiation request $R_A$ due to a certain situation, for example, if a patient's condition has changed suddenly or if the irradiation request $R_A$ has been erroneously transmitted. If it is determined that the beam scheduler 1 has received a cancellation request, the irradiation request R is deleted from the waiting list (Step S7) By deleting the unnecessary irradiation request $R_A$ from the waiting list, the beam can be efficiently allocated. After Step S7, the beam scheduler 1 ends the processing relating to the irradiation request $R_A$.

Figure 5:
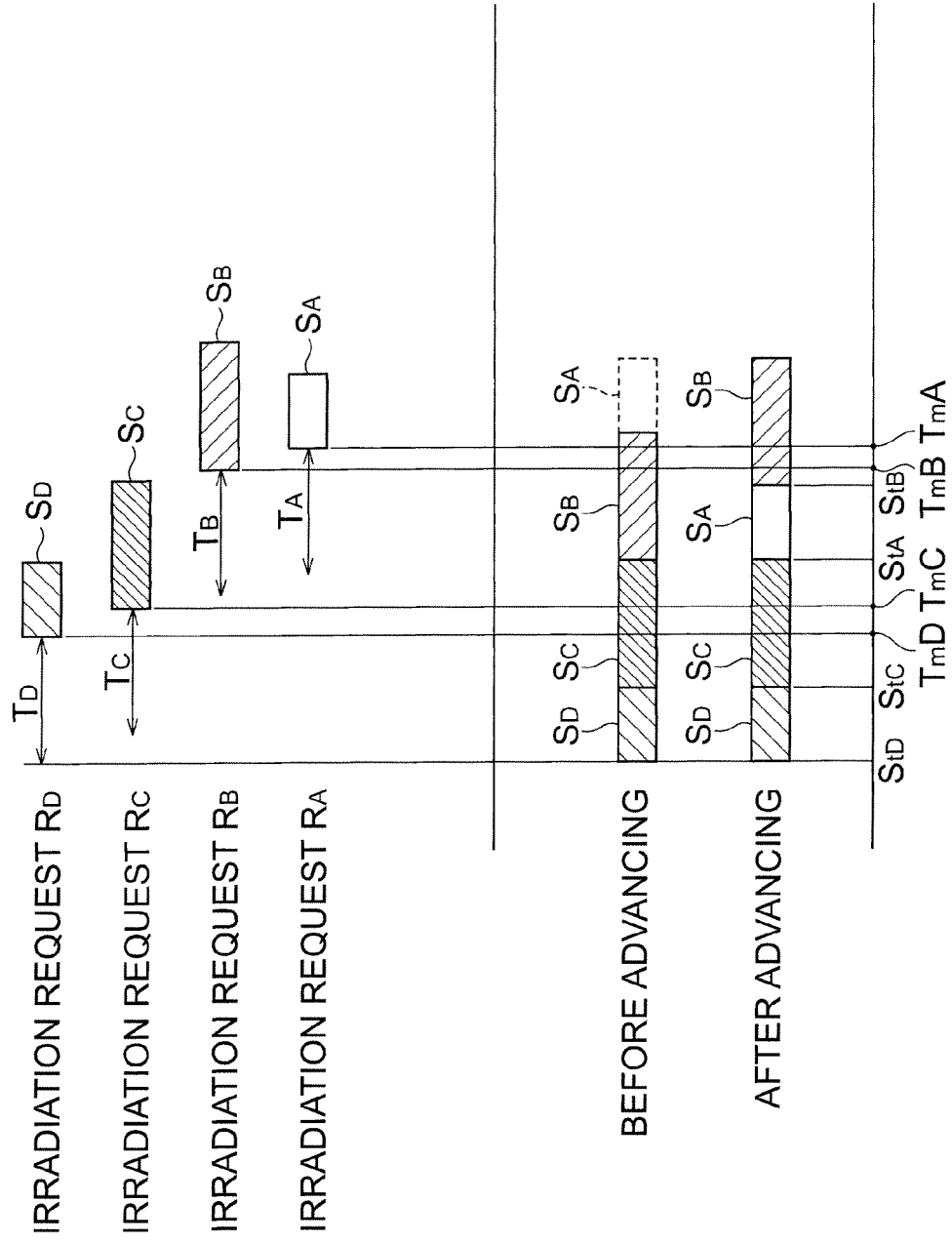
FIG. 5 is a view for describing the relation between the predicted waiting time of an irradiation request which is predicted and a maximum allowable waiting time.

If it is determined that any cancellation request is not received in Step S6, the beam scheduler 1 predicts the predicted waiting time of the irradiation request $R_A$ utilizing the total of the predicted required time of irradiation requests $R_B$ to $R_D$ which have the preceding order on the waiting list, and determines whether or not the predicted waiting time of the irradiation request $R_A$ predicted exceeds the maximum allowable waiting time (Step S8). This Step S8 is equivalent to a determination step in the claims. FIG. 5 is a view for describing the relationship between the predicted waiting time of an irradiation request which is predicted and the maximum allowable waiting time. In FIG. 5, $T_A$ to $T_D$ respectively show the maximum allowable waiting times added to the irradiation requests $R_A$ to $R_D$, and $S_A$ to $S_D$ respectively show the predicted required times added to the irradiation requests $R_A$ to $R_D$. Additionally, $S_{tA}$ to $S_{tD}$ respectively show time points which are predicted for the beam to be allocated to the respective irradiation chambers A to D, and $T_{mA}$ to $T_{mD}$ respectively show the time points when the maximum allowable waiting times $T_A$ to $T_D$ end.

As shown in FIGS. 4 and 5, when the irradiation requests $R_A$ to $R_D$ are arranged in the received order on the waiting list, the beam scheduler 1 allocates the beam in order of the irradiation chamber D, the irradiation chamber C, the irradiation chamber B, and the irradiation chamber A (see "before advancing" of FIG. 5). In this case, in the irradiation request $R_A$, since the time point $S_{tA}$, which is predicted for the beam to be allocated to the irradiation chamber A exceeds the time point $T_{mA}$ when the maximum allowable waiting time $T_A$ ends, the beam scheduler 1 determines that the predicted waiting time exceeds the maximum allowable waiting time $T_A$. On the other hand, in the irradiation request $R_C$, since the time point $S_{tC}$ which is predicted for the beam to be allocated to the irradiation chamber C does not exceed the time point $T_{mC}$ when the maximum allowable waiting time $T_C$ ends, the beam scheduler 1 determines that the predicted waiting time does not exceed the maximum allowable waiting time $T_C$.

In Step S8 of FIG. 3, if it is determined that the predicted waiting time of the irradiation request $R_A$ which is predicted does not exceed the maximum allowable waiting time, the beam scheduler 1 ends the processing relating to the irradiation request $R_A$ once.

On the other hand, if it is determined that the predicted waiting time of the irradiation request $R_A$ which is predicted exceeds the maximum allowable waiting time, the beam scheduler 1 determines whether or not advancing the order of the irradiation request $R_A$ is possible when it is determined that the predicted waiting time exceeds the maximum allowable waiting time (Step S9). Specifically, as shown in FIG. 5, if it is determined that the predicted waiting time of the irradiation request $R_A$ which is predicted exceeds the maximum allowable waiting time, when the order of the irradiation request $R_A$ is advanced ahead of the irradiation request $R_B$, the beam scheduler 1 determines that advancing is possible if the predicted waiting time of the irradiation request $R_B$ does not exceed the maximum allowable waiting time $T_B$, and determines that advancing is impossible if the predicted waiting time of the irradiation request $R_B$ exceeds the maximum allowable waiting time $T_B$.

Here, in the case shown in FIG. 5, even if advancing of the irradiation request $R_A$ is performed, a state where the time point $S_{tB}$ precedes the time point $T_{mB}$ is maintained in the irradiation request $R_B$, and the predicted waiting time of the irradiation request $R_B$ does not exceed the maximum allowable waiting time $T_B$. Thus, the beam scheduler 1 determines that advancing the order of irradiation request $R_A$ is possible. As a result of this advancing, the time point $S_{tA}$ does not exceed the time point $T_{mA}$ even in the irradiation request $R_A$, and the predicted waiting time no longer exceeds the maximum allowable waiting time $T_A$. In this way, a proper adjustment of the order in which the beam is allocated is realized between the irradiation request $R_A$ when the maximum allowable waiting time $T_A$ is comparatively short, and the irradiation request $R_B$ which has a margin in the maximum allowable waiting time $T_B$. As a result, in the case shown in FIG. 5, beam allocation of all the irradiation requests $R_A$ to $R_D$ becomes possible within the maximum allowable waiting time, and a situation where a healthcare practitioner or a patient is kept waiting for a longtime exceeding the maximum allowable waiting time can be avoided.

In Step S9 of FIG. 3, if it is determined that advancing the order of the irradiation request $R_A$ is possible, the beam scheduler 1 performs the advancing process which advances the order of the irradiation request $R_A$ (Step S10). This Step S10 is equivalent to an order changing step in the claims. Thereafter, the beam scheduler 1 ends the processing relating to the irradiation request $R_A$ once.

On the other hand, if advancing the order of an irradiation request for which it is determined that the predicted waiting time exceeds the maximum allowable waiting time is impossible, the beam scheduler 1 extends the maximum allowable waiting time of the irradiation request $R_A$ (Step S11). Specifically, if it is determined that advancing is impossible, the maximum allowable waiting time is extended so as to become longer than the total of the predicted required time of the irradiation requests which have higher priority in the order than the irradiation request $R_A$ on the waiting list, that is, the predicted waiting time of the irradiation request $R_A$ which is predicted. If the maximum allowable waiting time is extended, notification of the maximum allowable waiting time after the extension is sent to the irradiation chamber A which has issued the irradiation request $R_A$. Thereafter, the beam scheduler 1 ends the processing relating to the irradiation request $R_A$ once.

The processing of the beam scheduler when an irradiation request $R_A$ is located at the top of the order of the waiting list will be described.

Figure 6:
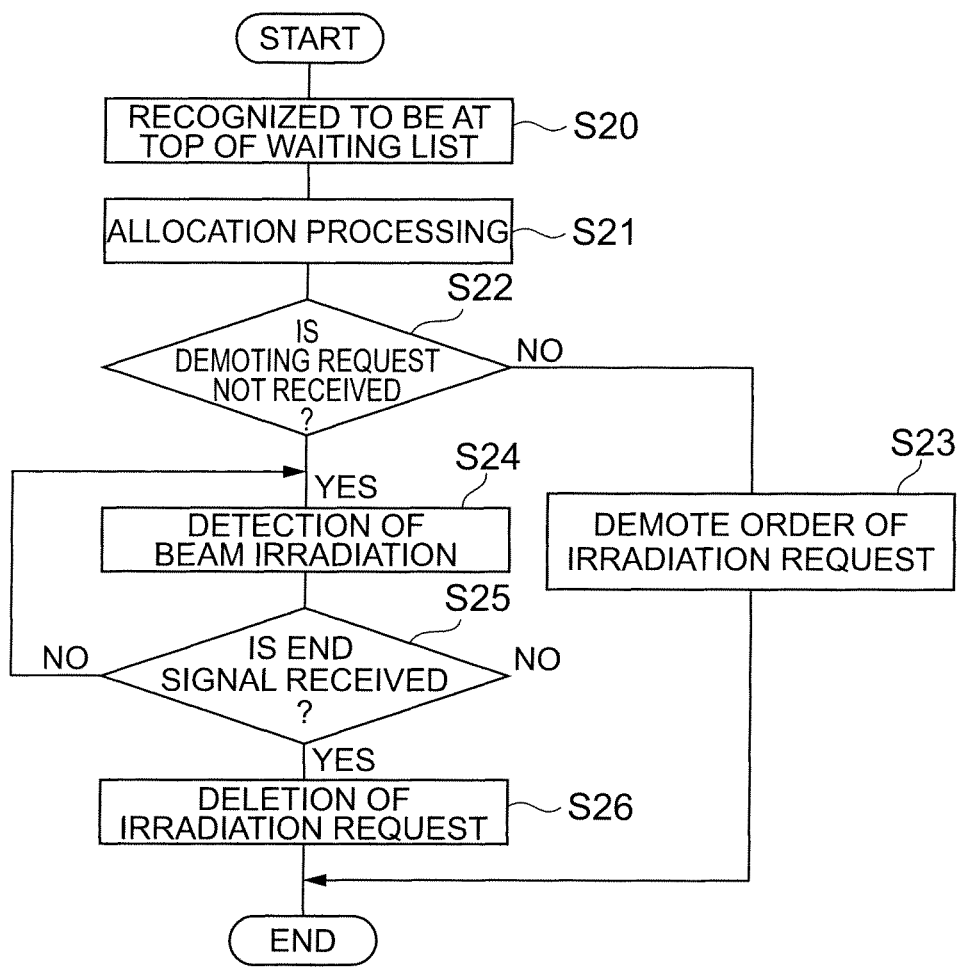
FIG. 6 is a flow chart showing the processing of a beam scheduler when an irradiation request is located at the top of the order of a waiting list.

As shown in FIG. 6, the beam scheduler 1 first recognizes that the irradiation request $R_A$ is located at the top of the order of the waiting list (Step S20). Thereafter, the beam scheduler 1 allocates the beam to the irradiation chamber A which has issued the irradiation request $R_A$ (Step S21). This Step S21 is equivalent to an allocation step in the claims.

After the allocation of the beam, it is determined whether or not the beam scheduler 1 has received a demoting request which demotes the order of irradiation request $R_A$ (Step S22). Such a demoting request is used, for example, when it is intended to suspend use of the beam temporarily, and is transmitted to the beam scheduler 1 as a healthcare practitioner operates the terminal 3.

If it is determined that a advancing request has been received, the beam scheduler 1 exchanges the position of the irradiation request $R_A$ located at the top of the order of the waiting list with the position of an irradiation request located at the position next to the irradiation request $R_A$ on the waiting list (Step S23). Thereafter, the beam scheduler 1 suspends the processing relating to the irradiation request $R_A$ until the beam scheduler recognizes again that the irradiation request $R_A$ is located at the top of the order of the waiting list. As the irradiation chamber A to which the beam is allocated issues a demoting request in this way, replacement can be made by yielding allocation of the beam to the irradiation chamber B of the next order, and thereby the medical treatment time can be adjusted. As a result, a situation where the allocation time of the beam is extended for reasons of waiting for stabilization of a patient's condition can be avoided, and efficient utilization of the particle beam irradiation facility 10 can be achieved.

On the other hand, if it is determined in Step S22 that a demoting request is not received, beam irradiation to a patient within the irradiation chamber A is started, and the beam scheduler 1 detects the irradiation of the beam (Step S24). The beam scheduler 1 determines whether or not an end signal relating to the end of use of the beam has been received from the irradiation chamber A to which the beam is allocated, after the irradiation of the beam is detected (Step S25). The end signal is automatically transmitted to the beam scheduler 1 when the irradiation with a preset amount of energy is ended. Additionally, the end signal can also be transmitted through the operation of a healthcare practitioner. If it is determined that the end signal is not received, the beam scheduler 1 returns to Step S24 from which processing is repeated again. Here, if an end time point of the predicted required time is approached while the end signal is not input, the beam scheduler 1 may perform warning processing to the irradiation chamber A through the terminal 3. If medical treatment time is likely to exceed the predicted required time, a healthcare practitioner, for example, can contact an operator in the main control room 12, thereby having the operator perform time adjustment or the like with other irradiation chambers.

If it is determined in Step S25 that the end signal is received, the beam scheduler 1 determines that the use of the beam in the irradiation chamber is ended and the irradiation request $R_A$ is deleted from the waiting list (Step S26). Thereafter, the beam scheduler 1 ends the processing relating to the irradiation request R.

According to the beam scheduler 1 related to the present embodiment described above, if it is determined that the predicted waiting time of an irradiation request exceeds the maximum allowable waiting time, a situation where a healthcare practitioner, such as a doctor, or a patient is kept waiting for a long time exceeding the maximum allowable waiting time can be avoided by advancing the irradiation request up the order of the waiting list. Thereby, a situation where medical treatment is postponed due to changes in a patient's condition during prolonged waiting can be avoided, and efficient utilization of the particle beam irradiation facility 10 can be achieved. Moreover, it is possible for a healthcare practitioner to make prediction that the beam will be allocated in the maximum allowable waiting time, and prepare medical treatment appropriately. This contributes to an increase in efficiency of utilization of the particle beam irradiation facility 10.

Additionally, according to the beam scheduler 1, it is determined that advancing is impossible if the predicted waiting time of the other irradiation requests exceeds the maximum allowable waiting time by advancing, and the maximum allowable waiting time is extended so as to become longer than the predicted waiting time of the predicted irradiation request. Thereby, a situation where the predicted waiting time of the other irradiation requests exceeds the maximum allowable waiting time by advancing can be avoided, and it is possible for a healthcare practitioner to make a prediction relating to the time when the beam will be allocated on the basis of the maximum allowable waiting time after extension.

Additionally, according to the beam scheduler 1, since interruption is not made unless a demoting request or the like is performed from the irradiation chambers once the beam is allocated, a healthcare practitioner can concentrate on medical treatment without concern about interruption.

The invention is not limited to the above-described embodiments.

For example, an aspect may be adopted in which, if the beam scheduler 1 determines in Step S9 that advancing is impossible, the beam scheduler 1 does not extend the maximum allowable waiting time automatically, but makes contact with an irradiation chamber where demoting is made by advancing an irradiation request of another irradiation chamber and the predicted waiting time exceeds the maximum allowable waiting time, and an irradiation chamber of an irradiation request which performs advancing, about the existence of an urgent irradiation request, and adjusts the order or maximum allowable waiting time between these irradiation chambers. Alternatively, an aspect may be adopted in which the beam scheduler 1 extends the maximum allowable waiting time of an irradiation request for which the maximum allowable waiting time is automatically set, i.e., an irradiation request which is not urgent, and preferentially performs advancing of an irradiation request manually input from a terminal of an irradiation chamber by a healthcare practitioner.

Additionally, the terminals 3 to 6 which input an irradiation request or the like to the beam scheduler 1 may be provided outside the irradiation chambers A to D, and may be provided at a separate facility connected to the particle beam irradiation facility 10 using a communication network. Similarly, the beam scheduler 1 is not limited to one which is realized within the main control unit 2 arranged at the main control room 12, and an aspect may be adopted in which the function of the beam scheduler is exhibited in cooperation with a computer which is arranged at a separate place. Additionally, the beam scheduler 1 does not need to have the function of replacing the order by a demoting request.

It should be understood that the invention is not limited to the above-described embodiment, but may be modified into various forms on the basis of the concept of the invention. Additionally, the modifications are included in the scope of the invention.

What is claimed is:

1. A beam scheduler which manages allocation of a beam to a plurality of irradiation chambers in a particle beam irradiation facility which supplies the beam to one irradiation chamber of the plurality of irradiation chambers, the beam scheduler comprising:
a maximum allowable waiting time addition unit which, if an irradiation request for the beam is received from one irradiation chamber of the plurality of irradiation chambers, adds a maximum allowable waiting time until the beam is allocated to the one irradiation chamber to the irradiation request;
an irradiation request managing unit which adds the irradiation request to the end of the order of a waiting list;
a determination unit which determines whether or not a predicted waiting time until the beam is allocated to the one irradiation chamber exceeds the maximum allowable waiting time; and
an order changing unit which, if the determination unit has determined that the predicted waiting time exceeds the maximum allowable waiting time, advances the irradiation request up the order of the waiting list,
wherein the beam is allocated to the irradiation chamber corresponding to the top irradiation request in the order of the waiting list, and
wherein if the predicted waiting time of other irradiation requests exceeds a maximum allowable waiting time of the other irradiation requests due to advancing the order of the irradiation request, the order changing unit extends the maximum allowable waiting time of the irradiation request without advancing.

2. The beam scheduler according to claim 1, further comprising a request deletion unit which, if a cancellation request is received from the irradiation chamber corresponding to the irradiation request arranged on the waiting list, deletes the irradiation request from the waiting list.

3. The beam scheduler according to claim 1,
wherein if a demoting request which demotes the order of the irradiation request is received from the irradiation chamber to which the beam is allocated, the order changing unit exchanges the position of the irradiation request located at the top of the order of the waiting list, and the irradiation request located next in the order.

4. A beam allocation method for a beam scheduler which manages allocation of a beam to a plurality of irradiation chambers in a particle beam irradiation facility which supplies the beam to one irradiation chamber of the plurality of irradiation chambers, the beam allocation method comprising:
a maximum allowable waiting time adding step of adding a maximum allowable waiting time until the beam is allocated to the one irradiation chamber to the irradiation request if an irradiation request for the beam is received from the one irradiation chamber of the plurality of irradiation chambers;
an irradiation request management step of adding the irradiation request to the end of the order of a waiting list;

a determination step of determining whether or not a predicted waiting time until the beam is allocated to the one irradiation chamber exceeds the maximum allowable waiting time;

an order changing step of advancing irradiation request up the order of the waiting list if it is determined that the predicted waiting time exceeds the maximum allowable waiting time in the determination step; and an allocation step of allocating the beam to the irradiation chamber corresponding to the top irradiation request in the order of the waiting list, wherein if the predicted waiting time of other irradiation requests exceeds a maximum allowable waiting time of the other irradiation requests due to advancing the order of the irradiation request, the order changing unit extends the maximum allowable waiting time of the irradiation request without advancing.

* * * * *